United States Patent
Cook et al.

(10) Patent No.: US 8,133,257 B2
(45) Date of Patent: Mar. 13, 2012

(54) BIOABSORBABLE SUTURE ANCHOR SYSTEM FOR USE IN SMALL JOINTS

(75) Inventors: Shelby L. Cook, Mansfield, MA (US); Jose E. Lizardi, Franklin, MA (US); Karl S. Reese, Boston, MA (US); Thomas A. Shepard, Buford, GA (US)

(73) Assignee: DePuy Mitek, Inc., Raynham, MA (US)

( * ) Notice: Subject to any disclaimer, the term of this patent is extended or adjusted under 35 U.S.C. 154(b) by 734 days.

(21) Appl. No.: 10/615,625

(22) Filed: Jun. 27, 2003

(65) Prior Publication Data

US 2005/0019368 A1    Jan. 27, 2005

(51) Int. Cl.
A61B 17/04    (2006.01)

(52) U.S. Cl. .......................... 606/232; 606/300
(58) Field of Classification Search .................. 606/72, 606/75, 73, 232, 222, 223, 300
See application file for complete search history.

(56) References Cited

U.S. PATENT DOCUMENTS

| | | | |
|---|---|---|---|
| 4,321,038 A * | 3/1982 | Porteous ............... | 433/136 |
| 5,203,787 A | 4/1993 | Noblitt et al. | |
| 5,464,425 A | 11/1995 | Skiba | |
| 5,522,845 A | 6/1996 | Wenstrom, Jr. | |
| 5,540,718 A | 7/1996 | Bartlett | |
| 5,611,814 A | 3/1997 | Lorenc | |
| 5,626,612 A * | 5/1997 | Bartlett ................ | 606/232 |
| 5,683,418 A | 11/1997 | Luscombe et al. | |
| 5,782,863 A | 7/1998 | Bartlett | |
| 5,814,072 A | 9/1998 | Bonutti | |
| 5,871,503 A | 2/1999 | Bartlett | |
| 5,873,891 A | 2/1999 | Sohn | |
| 5,879,372 A | 3/1999 | Bartlett | |
| 5,894,921 A | 4/1999 | Le et al. | |
| 5,950,633 A | 9/1999 | Lynch et al. | |
| 5,961,538 A | 10/1999 | Pedlick et al. | |
| 6,146,408 A | 11/2000 | Bartlett | |

(Continued)

FOREIGN PATENT DOCUMENTS

EP    1 297 788 A2    4/2003

(Continued)

OTHER PUBLICATIONS

Barroso, E. et al., "Surgical Technique: Endoscopic Browlift with Rigid Fixation Using the Mitek 2.0 mm Tacit™ Threaded Anchor," Mitek Surgical Products, Inc. (1997).

(Continued)

Primary Examiner — Tuan Nguyen

(57) ABSTRACT

A bioabsorbable suture anchor for anchoring soft tissue to a bone is provided. The suture anchor is configured to toggle and anchor itself inside a bone cavity of a small joint. The anchor comprises an elongate body defined by a longitudinal axis, a first, leading end and a second, trailing end. The elongate body also has two opposed surfaces between the first and second ends, and a plurality of sidewalls extending between the two opposed surfaces. Extending from one of the sidewalls is a flared portion that is formed on the second end of the elongate body. The flared portion is adapted to engage and anchor into bone tissue upon toggling. A suture channel extends between the two opposed surfaces. The suture channel is formed in the elongate body for passage of a suture strand therethrough, such that pulling on an attached suture strand effects toggling of the anchor inside a bone cavity.

17 Claims, 4 Drawing Sheets

U.S. PATENT DOCUMENTS

| | | | |
|---|---|---|---|
| 6,270,518 B1 * | 8/2001 | Pedlick et al. | 606/232 |
| 6,280,474 B1 * | 8/2001 | Cassidy et al. | 623/16.11 |
| 6,306,158 B1 | 10/2001 | Bartlett | |
| 6,773,436 B2 * | 8/2004 | Donnelly et al. | 606/72 |
| 7,232,455 B2 * | 6/2007 | Pedlick et al. | 606/232 |
| 2002/0004469 A1 | 1/2002 | Faber | |
| 2002/0007196 A1 | 1/2002 | Bartlett | |
| 2002/0099411 A1 | 7/2002 | Bartlett | |

FOREIGN PATENT DOCUMENTS

| | | |
|---|---|---|
| JP | 8-52155 | 2/1996 |
| JP | 2002-537886 | 11/2002 |
| JP | 2003-153916 | 5/2003 |

OTHER PUBLICATIONS

Brewer, K., "Endoscopic Brow Lifts," Assoc. Plastic Surgery Assts Network Publ. 12(1):13-15 (1997).

Kozin, S., "Treatment of Thumb Ulnar Collateral Ligament Ruptures with the Mitek Bone Anchor," Ann. Plastic Surgery 35(1):1-5 (1995).

Mitek Products, Product Reference Guide.

Product Brochure for *Mitek® 1.3 mm Micro Anchor*, Mitek Surgical Products, Inc. (1997).

Product Brochure for *Mitek® 2.0 mm Tacit™ Threaded Anchor*, Mitek Surgical Products, Inc. (1996).

Product Brochure for *Bioknotless™ Anchor*, Mitek Products.

Product Brochure for *Bioknotless RC Anchor*, Mitek Worldwide.

Product Brochure for *Bioknotless™ Suture Anchor*, Mitek Products.

Product Brochure for *MicroFix™* DePuy Mitek.

Product Brochure for *Panalok® RC*, Mitek Products.

Rokkanen P. et al., "Biofix® Ligament Tack: Biodegradable Ligament Injury Fixation Tacks Surgical Techniques I," Helsinki Univ. Central Hosp. Dept Ortho. & Traum. (1990).

Short W., "Surgical Technique: Scapholunate Surgical Technique Using the Mitek 2.0 mm Tacit™ Threaded Anchor," Mitek Surgical Products, Inc. (1996).

* cited by examiner

BIOABSORBABLE SUTURE ANCHOR SYSTEM FOR USE IN SMALL JOINTS

CROSS-REFERENCE TO RELATED APPLICATIONS

Not applicable.

STATEMENT REGARDING FEDERALLY SPONSORED RESEARCH

Not Applicable.

FIELD OF THE INVENTION

The invention relates generally to medical devices and procedures. Particularly, this invention relates to a bioabsorbable suture anchor system for attaching soft tissue to hard bone, and to methods for attaching soft tissue to hard bone. More particularly, the invention relates to a bioabsorbable suture anchor system configured for use in hand and craniofacial surgery.

BACKGROUND OF THE INVENTION

Soft tissues, such as ligaments, tendons and muscles, are attached to a large portion of the human skeleton. In particular, many ligaments and tendons are attached to the bones which form joints, such as shoulder and knee joints. A variety of injuries and conditions require attachment or reattachment of a soft tissue to bone. For example, when otherwise healthy tissue has been torn away from a bone, surgery is often required to reattach the tissue to the bone to allow healing and a natural reattachment to occur.

A number of devices and methods have been developed to attach soft tissue to bone. These include screws, staples, cement, suture anchors, and sutures alone. Some of the more successful methods involve use of a suture anchor to attach a suture to the bone, and tying the suture in a manner that holds the tissue in close proximity to the bone.

The tissue may be attached to the bone during open surgery, or during closed (e.g., arthroscopic) surgical procedures. Closed surgical procedures are preferred since they are less invasive and are less likely to cause patient trauma. In a closed surgical procedure, the surgeon performs diagnostic and therapeutic procedures at the surgical site through small incisions, called portals, using instruments specially designed for this purpose. One problem encountered in the less invasive, closed surgical procedures is that the surgeon has significantly less room to perform the required manipulations at the surgical site. Thus, devices and methods are needed which will allow a surgeon to effectively and easily attach tissue to bone in the small spaces provided by less invasive surgical procedures.

Suture anchors for reattaching soft tissue to bone are known in the art. However, these suture anchors are typically sized and dimensioned for use in large bone joints such as the patient's shoulder or knee. Where there is a need to reattach tissue to a relatively small bone in the patient's body, such as in the hand or the skull, the anchors currently available would be too large for the insertion depth desired. There is thus a need for a suture anchor that is suitably dimensioned and configured for reattaching soft tissue to bone in small joints of the patient such as in the hand or skull.

SUMMARY OF THE INVENTION

The present invention provides a system for anchoring soft tissue to bone using a bioabsorbable suture anchor for anchoring soft tissue to a bone of a small joint. The suture anchor is configured to toggle and anchor itself inside a bone cavity of a small joint. The anchor comprises an elongate body defined by a longitudinal axis, a first, leading end and a second, trailing end. The elongate body also has two opposed surfaces extending between the first and second ends, and a plurality of sidewalls extending between the two opposed surfaces. The first, leading end can be tapered and extend into a blunt tip having a continuous surface, while the second, trailing end can be wider than the first end such that one of the sidewalls is flared. In one aspect of the present invention, the blunt tip of the first, leading end can have a smooth outer edge.

The suture anchor also includes a suture channel that extends between the two opposed surfaces. The suture channel is formed in the elongate body to allow the passage of a suture strand therethrough, and it is preferably oriented to be transverse to the longitudinal axis of the anchor. The suture channel is flanked, or bordered on each side by an opening that is located on an opposed surface. To enable the suture strand to glide smoothly around the suture channel, the openings can be provided with rims that are flared or chamfered so as to avoid snagging or cutting the suture strand on a sharp edge of the opening as the suture strand passes back and forth within the suture channel. The center of each of the openings can be longitudinally offset with respect to the longitudinal axis of the elongate body. The offset channel enables a surgeon to toggle the suture anchor by pulling on an attached suture strand while the anchor is inside a bone cavity.

Additionally, the suture anchor of the present invention can also be provided with a bore extending into the elongate body from the second, trailing end thereof. An insertion tool can be attached to the bore of the anchor. Preferably, the bore and insertion tool form a slip fit, or interference fit, with one another.

The suture anchor of the present invention is sized and configured for insertion in a small bone such as would be found in the hand or skull. The length of the elongate body can be in the range of about 2 to about 6 mm, while the width of the second, trailing end of the anchor is about 1 to about 3 mm at its widest portion, tapering to a smaller width at the first, leading end.

In yet another aspect of the present invention, the flared portion has a shape effective to penetrate into bone. For instance, the flared portion can include a sharp edge for digging into bone tissue. Additionally, the flared portion can include a flat, bone-contacting face with a knife edge that is able to cut into bone tissue and secure the suture anchor within a bone cavity.

Also provided is a system for anchoring tissue to a bone of a small joint. The system includes a bioabsorbable suture anchor as described above with a loop of suture thread attached thereto. A suture anchor insertion tool can also be provided with the present system. The insertion tool is an elongate member with a proximal, handle end and a distal, attachment end that includes an insertion tip configured to provide an interference fit with the bore of the suture anchor.

Further features of the invention, its nature and various advantages, will be more apparent from the accompanying drawings and the following detailed description of the drawings and the preferred embodiments.

BRIEF DESCRIPTION OF THE DRAWINGS

The invention can be more fully understood from the following detailed description taken in conjunction with the accompanying drawings, in which.

DETAILED DESCRIPTION OF THE INVENTION

Figure 1:
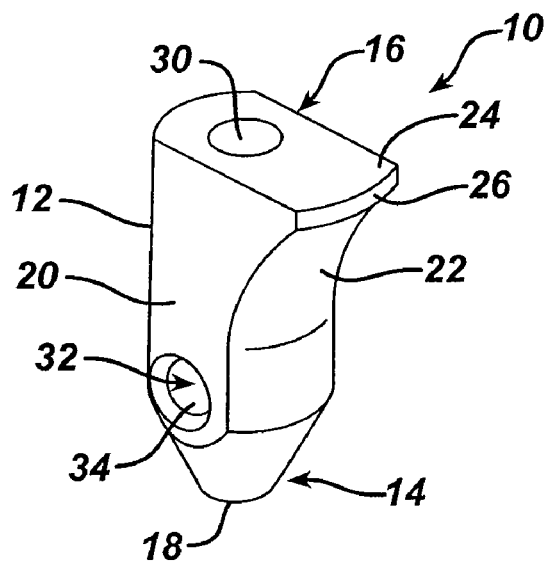
FIG. 1 is a perspective view of a suture anchor of the present invention.

Referring to FIG. 1, an exemplary suture anchor 10 of the present invention is shown having an elongate body 12 extending between a first, leading end 14 and a second, trailing end 16 for defining a longitudinal axis L. The first, leading end 14 may be tapered as shown, and can extend into a blunt tip 18 having a continuous surface. Preferably, the blunt tip 18 has a smooth outer edge. Extending between the first and second ends 14, 16 are a pair of opposed surfaces 20 and a plurality of sidewalls 22 adjacent to and extending between the two opposed surfaces 20, which together define the elongate body 12. Near the second, trailing end 16 and extending from one of the plurality of sidewalls 22 is a flared portion 24. The flared portion 24 lends an asymmetric profile to the suture anchor 10 and facilitates the toggling action of the suture anchor 10 once inserted inside a bone cavity. The flared portion 24 also has a shape that is effective to penetrate into bone. For instance, the flared portion 24 can have a sharp edge for penetrating into bone tissue. As illustrated, the flared portion 24 can also include a flat, bone-contacting face 26 having a knife edge to effectively engage the walls of the bone cavity.

Although surfaces 20 are shown as flat, it is understood that they may be otherwise shaped or contoured. For example, the surfaces 20 can be curved or rounded. Opposed surfaces 20 can also include surface features such as roughened portions, or protrusions, that facilitate anchorage of the suture anchor 10 into the bone cavity. The sidewalls 22 that are adjacent to the opposed surfaces 20 can also be curved, rounded, or flat. Preferably, the sidewalls 22 are generally concavely shaped. As illustrated in FIG. 1, a bore 30 extends from the second trailing end 16 into the elongate body 12. The bore 30 is configured to engage a proximal end of an inserter tool. The bore 30 can be configured to provide an interference, or slip fit, with an inserter tip of an inserter tool, such as the one shown in FIGS. 5B and 6B.

Figure 2A:
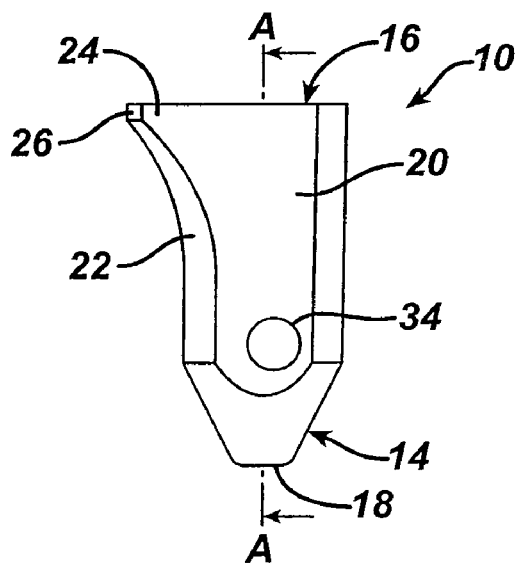
FIG. 2A is a side view of the suture anchor of FIG. 1.
Figure 2B:
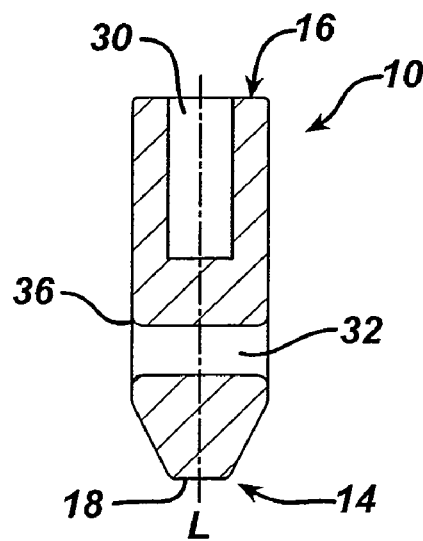
FIG. 2B is a cross-sectional view of the suture anchor of FIG. 2B along lines A-A.

The elongate body 12 also includes a suture channel 32 for passage of a suture strand through the suture anchor 10. As shown in FIG. 2B, the suture channel 32 extends in a direction transverse to the longitudinal axis L of the elongate body 12 and through each of the opposed surfaces 20 of suture anchor 10. The suture channel 32 is flanked, or bordered on each side by an opening 34 that is located on an opposed surface 20. To enable an attached suture strand to glide smoothly around the suture channel 32, the openings can be provided with a rim 36 that has a smooth, or flared, edge so as to avoid snagging or cutting the suture strand on a sharp edge of the opening 34 as the suture strand is passed back and forth within the suture channel 32. As illustrated in FIG. 2A, a center of the opening 34 is longitudinally offset with respect to the longitudinal axis L of the body 12. Preferably, the center of the opening 34 is located away from the longitudinal axis L on the side of the axis opposite the flared portion 24. The offset suture channel 32 enables a surgeon to toggle the suture anchor 10 by pulling on an attached suture strand when the suture anchor 10 is inside a bone cavity.

Figure 3:
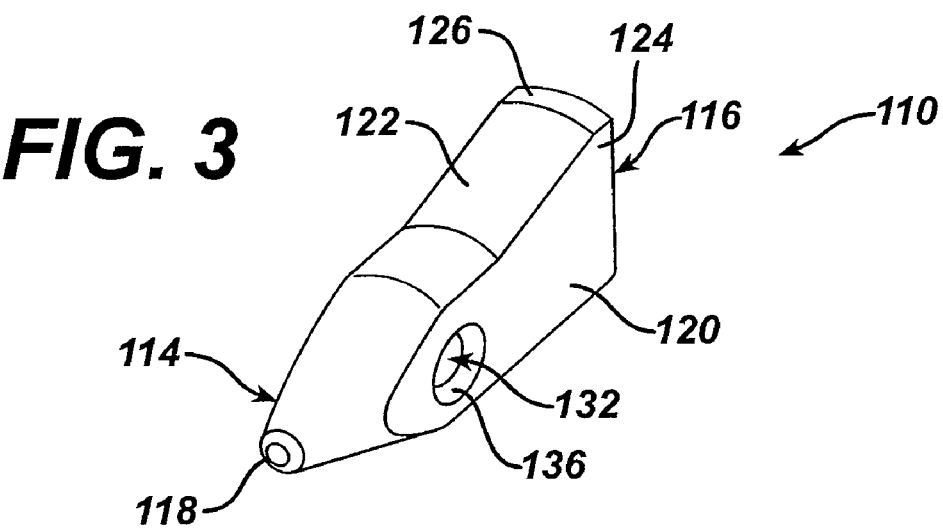
FIG. 3 is a perspective view of another embodiment of a suture anchor of the present invention.
Figure 4A:
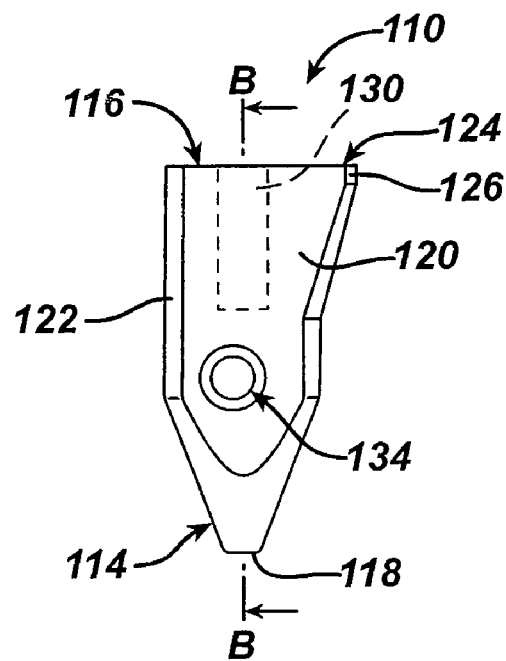
FIG. 4A is a side view of the suture anchor of FIG. 3.
Figure 4B:
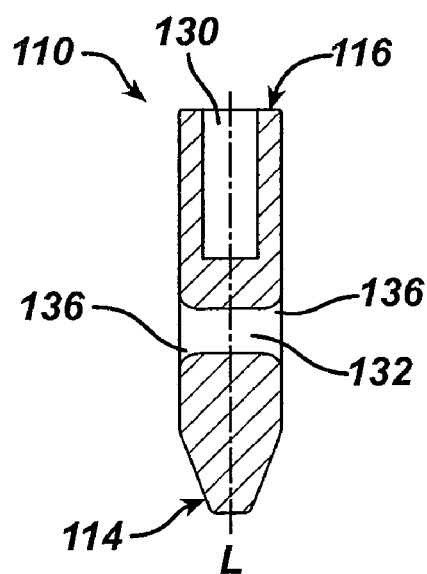
FIG. 4B is a cross-sectional view of the suture anchor of FIG. 4B along lines B-B.

FIG. 3 shows another exemplary embodiment of a suture anchor 110 the present invention. Suture anchor 110 is similar to suture anchor 10 and shares similar features, which are labeled by the same numeral with the prefix "1" for convenient reference. Similar to the previous embodiment described, the openings 134 of the suture channel 132 of the suture anchor 110 are also longitudinally offset with respect to a longitudinal axis L of the elongate body 112, as illustrated in FIG. 4A. However, in suture anchor 110, the rim 136 of each opening 134 is chamfered. As shown in FIG. 4B, the rim 136 can be chamfered at an angle of about 45°. It is contemplated that the chamfered openings 134 help enable as much of the suture strand to lie flush with respect to opposed surfaces 120 as possible, alleviating suture binding and pinching of the suture strand between the bone cavity and the suture anchor 110.

The suture anchors 10, 110 of the present invention are configured and sized such that they can be used, with sutures, in the repair or reconstruction of collateral ligaments, flexor and extensor tendon at the proximal interphalangeal (PIP), distal interphalangeal (DIP), and metacarpal interphalangeal (MIP) joints of all digits in a patient's hand. Additionally, these anchors 10, 110 can be used to attach soft tissue to the parietal, temporal ridge, frontal, mandible, maxilla, zygoma, and periorbital bones of the skull. Therefore, the suture anchors 10, 110 should have a length sufficient to enable them to properly seat within a small bone such as those mentioned, but be sized and configured to be effective in a surgery to reattach soft tissue to such bone. To this end, the suture anchors 10, 110 of the present invention have a length in the range of about 2 to about 6 mm. Additionally, the width of the second, trailing end 16, 116 is in the range of about 1 to about 3 mm at its widest portion. It is contemplated that suture anchors 10, 110 dimensioned within these ranges are suitable for use in a bone cavity that is no more than about 5 to 10 mm in depth.

Because of the reduced size of the anchors 10, 110, the elongate body 12, 112 can include a visualization aid to assist the surgeon in locating the suture anchor 10, 110. In one exemplary embodiment, the elongate body 12, 112 of the suture anchor 10, 110 can be formed from a polymeric material which has incorporated therein blue dye #6 which gives the anchor 10, 110 a blue tint.

Furthermore, while suture anchors 10, 110 are illustrated with blunt tips 18, 118, it is understood that the first, leading ends 14, 114 can be provided with tips having other configurations as well. For instance, the tips of the anchors 10, 110 can be sharp or pointed, or can include protrusions or roughened surface features to facilitate engagement with bone tissue as desired.

The suture anchors 10, 110 of the present invention are fully bioabsorbable. This provides the benefit of reducing immunological problems associated with having a foreign substance within the body over a prolonged period of time. It is contemplated that the bioabsorbable material can include a bioabsorbable, biocompatible polymer such as polylactic acid (PLA). However, it is understood that other suitable biocompatible, bioabsorbable polymers can also be used. Examples include polymers selected from the group consisting of aliphatic polyesters, poly(amino acids), copoly(etheresters), polyalkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, biomolecules (i.e., biopolymers such as collagen, elastin, bioabsorbable starches, etc.) and blends thereof. For the purpose of this invention aliphatic polyesters include, but are not limited to, homopolymers and copolymers of lactide (which includes lactic acid, D-,L- and meso lactide), glycolide (including glycolic acid), ε-caprolactone, p-dioxanone (1,4-dioxan-2-one), trimethylene carbonate (1,3-dioxan-2-one), alkyl derivatives of trimethylene carbonate, γ-valerolactone, β-butyrolactone, γ-butyrolactone, ε-decalactone, hydroxybutyrate, hydroxyvalerate, 1,4-dioxepan-2-one (including its dimer 1,5,8,12-tetraoxacyclotetradecane-7,14-dione), 1,5-dioxepan-2-one, 6,6-dimethyl-1,4-dioxan-2-one 2,5-diketomorpholine, pivalolactone, α,α-diethylpropiolactone, ethylene carbonate, ethylene oxalate, 3-methyl-1,4-dioxane-2,5-dione, 3,3-diethyl-1,4-dioxan-2,5-dione, 6,8-dioxabicycloctane-7-one and polymer blends thereof. Poly (iminocarbonates), for the purpose of this invention, are understood to include those polymers as described by Kemnitzer and Kohn, in the *Handbook of Biodegradable Polymers*, edited by Domb, et. al., Hardwood Academic Press, pp. 251-272 (1997). Copoly(ether-esters), for the purpose of this invention, are understood to include those copoly-ester-ethers as described in the Journal of Biomaterials Research, Vol. 22, pages 993-1009, 1988 by Cohn and Younes, and in Polymer Preprints (ACS Division of Polymer Chemistry), Vol. 30(1), page 498, 1989 by Cohn (e.g. PEO/PLA). Polyalkylene oxalates, for the purpose of this invention, include those described in U.S. Pat. Nos. 4,208,511; 4,141,087; 4,130,639; 4,140,678; 4,105,034; and 4,205,399. Polyphosphazenes, co-, ter- and higher order mixed monomer based polymers made from L-lactide, D,L-lactide, lactic acid, glycolide, glycolic acid, para-dioxanone, trimethylene carbonate and ε-caprolactone such as are described by Allcock in *The Encyclopedia of Polymer Science*, Vol. 13, pages 31-41, Wiley Intersciences, John Wiley & Sons, 1988 and by Vandorpe, et al in the *Handbook of Biodegradable Polymers*, edited by Domb, et al, Hardwood Academic Press, pp. 161-182 (1997). Polyanhydrides include those derived from diacids of the form HOOC—$C_6H_4$—O—$(CH_2)_m$—O—$C_6H_4$—COOH, where m is an integer in the range of from 2 to 8, and copolymers thereof with aliphatic alpha-omega diacids of up to 12 carbons. Polyoxaesters, polyoxaamides and polyoxaesters containing amines and/or amido groups are described in one or more of the following U.S. Pat. Nos. 5,464,929; 5,595,751; 5,597,579; 5,607,687; 5,618,552; 5,620,698; 5,645,850; 5,648,088; 5,698,213; 5,700,583; and 5,859,150. Polyorthoesters such as those described by Heller in *Handbook of Biodegradable Polymers*, edited by Domb, et al, Hardwood Academic Press, pp. 99-118 (1997).

Exemplary bioabsorbable, biocompatible elastomers include but are not limited to elastomeric copolymers of ε-caprolactone and glycolide (including polyglycolic acid) with a mole ratio of ε-caprolactone to glycolide of from about 35:65 to about 65:35, more preferably from 45:55 to 35:65; elastomeric copolymers of ε-caprolactone and lactide (including L-lactide, D-lactide, blends thereof, and lactic acid polymers and copolymers) where the mole ratio of ε-caprolactone to lactide is from about 35:65 to about 65:35 and more preferably from 45:55 to 30:70 or from about 95:5 to about 85:15; elastomeric copolymers of p-dioxanone (1,4-dioxan-2-one) and lactide (including L-lactide, D-lactide, blends thereof, and lactic acid polymers and copolymers) where the mole ratio of p-dioxanone to lactide is from about 40:60 to about 60:40; elastomeric copolymers of ε-caprolactone and p-dioxanone where the mole ratio of ε-caprolactone to p-dioxanone is from about from 30:70 to about 70:30; elastomeric copolymers of p-dioxanone and trimethylene carbonate where the mole ratio of p-dioxanone to trimethylene carbonate is from about 30:70 to about 70:30; elastomeric copolymers of trimethylene carbonate and glycolide (including polyglycolic acid) where the mole ratio of trimethylene carbonate to glycolide is from about 30:70 to about 70:30; elastomeric copolymers of trimethylene carbonate and lactide (including L-lactide, D-lactide, blends thereof, and lactic acid polymers and copolymers) where the mole ratio of trimethylene carbonate to lactide is from about 30:70 to about 70:30; and blends thereof.

The present invention also provides a system 200 for anchoring tissue to bone using suture anchors 10, 110. The exemplary suture anchor system 200 is described below, together with a typical procedure for using the suture anchors 10, 110 and system 200 of the invention. One skilled in the art will appreciate a procedure in which the suture anchor 10, 110 and system 200 of the invention first involves preparing the patient and then administering a suitable anesthetic. Thereafter, the surgical site is accessed by an appropriate surgical technique (e.g., open or closed surgery).

Figure 5A:
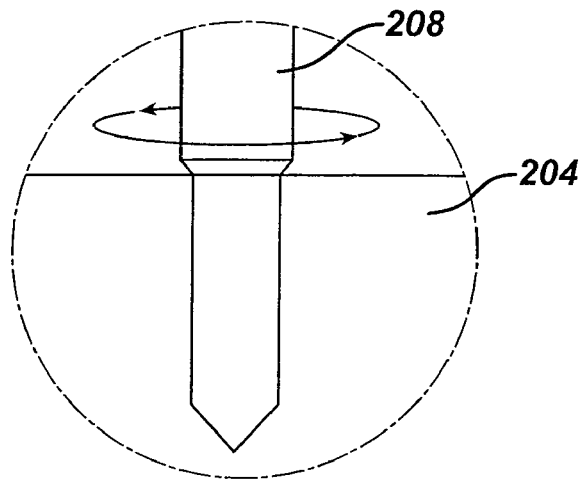
FIGS. 5A-5C illustrate an exemplary method for inserting the suture anchor of FIG. 1 in a patient.
Figure 5B:
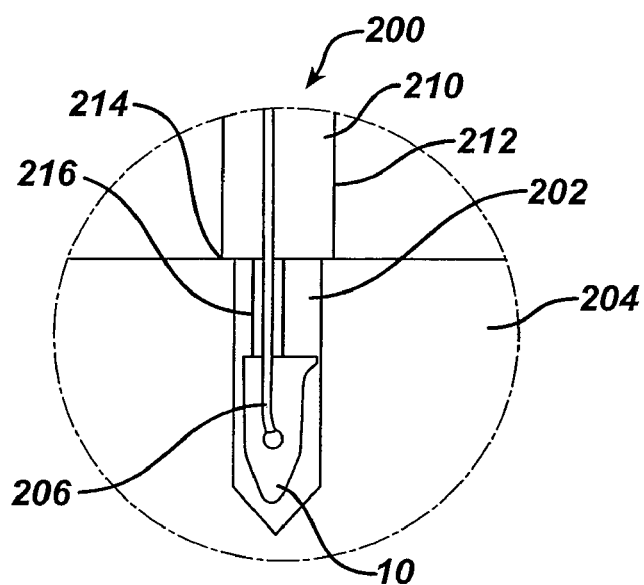

Referring to FIG. 5A, a bone cavity 202 is then formed in a bone 204 of a small joint using a sterile drill 208 (or other appropriate tool) as are well known in the surgical art. The diameter of the bone cavity 202 should be slightly smaller than the widest portion of the second, trailing end 16 of the suture anchor 10. In an exemplary embodiment, the diameter of the bone cavity 202 is in the range of approximately 1 to 3 mm, while the depth of the bone cavity is in the range of about 5 to about 10 mm. The depth of the bone cavity must be of sufficient length to allow for complete seating of the anchor 10. As shown in FIG. 5B, a suture anchor insertion tool 210 can be used to insert suture anchor 10 into the bone cavity 202. Insertion tool 210 is an elongate member 212 with a proximal, handle end (not shown) and a distal, attachment end 214 which includes an insertion tip 216 that is configured to provide an interference or slip fit with the bore 30 of the suture anchor 10.

Suture anchor 10 can be provided with an open suture, i.e., a suture strand extending therethrough, or with a suture having a needle (not shown) already attached for bringing soft tissue in proximity to the bony structure 204 for reattachment. The suture needle can have a first, tissue penetrating end and a second, trailing end attached to a loop of suture thread extending through suture anchor 10.

Figure 5C:
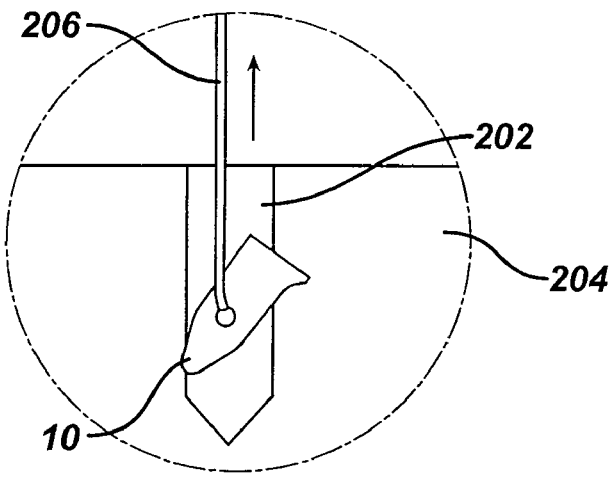

In FIG. 5C, the suture thread 206 extending from suture anchor 10 has been threaded through the free end of the tissue to be reattached using any conventional method known in the surgical art. Once the anchor 10 has been inserted inside the bone cavity 20, the inserter tool 210 can be removed by detaching the insertion tip 216 from the bore 30 of the anchor 10. The free ends of suture thread 206 can be pulled to apply tension to the suture 206 seated within the suture anchor 10. This tension will cause the anchor 10 to toggle and results in the flared portion 24 of the anchor 10 being lodged into the side of the bone cavity 202 as shown in FIG. 5C.

It is contemplated that toggling of the anchor 10 can also be achieved by mechanically deflecting the suture anchor 10 with the inserter tool 210. Both techniques can work in synchrony to create an optimal interference fit of the anchor 10 within the bone cavity 202.

Figure 6A:
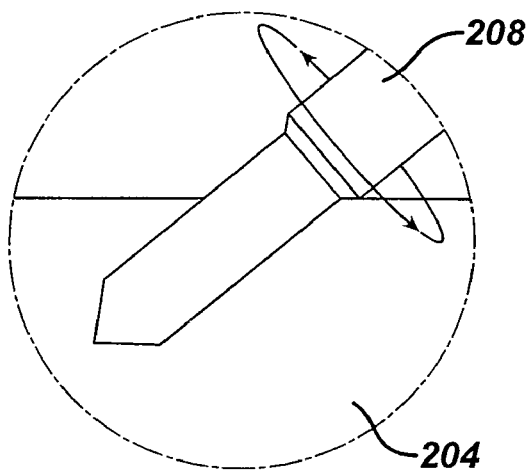
FIGS. 6A-6C illustrate yet another exemplary method for inserting the suture anchor of FIG. 1 in a patient.
Figure 6B:
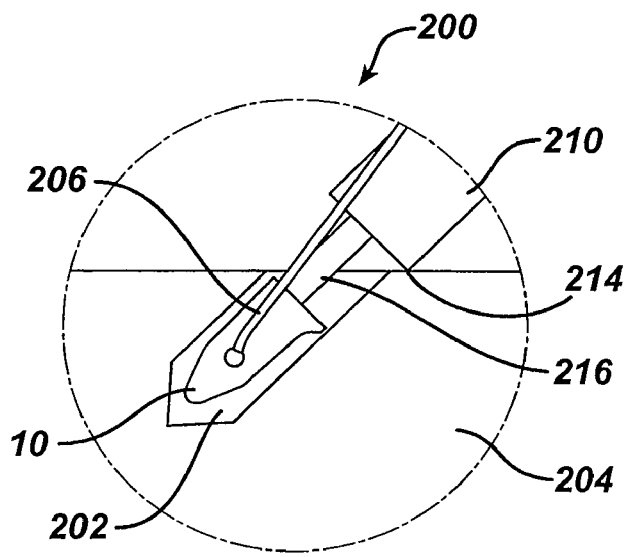
Figure 6C:
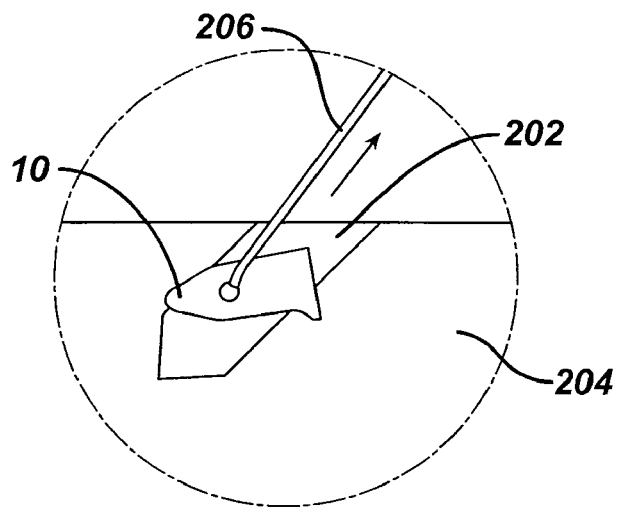

In yet another exemplary embodiment of the present invention, a method for using system 200 with suture anchor 10 is shown in FIGS. 6A-6C. As illustrated, a bone cavity 202 is drilled at about a 135° angle relative to the final orientation of the ligament/tendon after the repair. The insertion tool 210 with the attached suture anchor 10 is inserted into the bone cavity 202, and the attached suture strands pulled to effect toggling of the suture anchor 10 inside the bone cavity 202. Such a procedure is especially common where access to the bone can only be achieved at an angle, or where the bone does not have sufficient depth to allow the bone drill to be inserted straight down the bone surface. It is contemplated that this procedure would be effective for repairing torn tissue in hand bones.

It will be understood that the foregoing is only illustrative of the principles of the invention, and that various modifications can be made by those skilled in the art without departing from the scope and spirit of the invention. All references cited herein are expressly incorporated by reference in their entirety.

What is claimed is:

1. A suture anchor for anchoring tissue to a bone, comprising:
   an elongate body defined by a longitudinal axis of symmetry, a first, leading end and a second, trailing end, the elongate body comprising two opposed surfaces between the first and second ends, and a plurality of sidewalls extending between the two opposed surfaces;
   a flared portion formed on the second end and extending from one of the sidewalls, the flared portion being adapted to engage and anchor into bone tissue; and
   a suture channel formed in the elongate body for passage of a suture strand therethrough, the suture channel extending between the two opposed surfaces, being oriented substantially transverse at right angles to the longitudinal axis of symmetry of the body, and having a centerline that is transvers to and laterally offset with respect to the longitudinal axis of symmetry of the body in a direction opposite to the direction of the flared portion;
   wherein the suture anchor is configured to toggle and anchor inside a bone cavity based on tension being applied to a suture in the suture channel.

2. The anchor of claim 1, wherein a length of the elongate body is in the range of about 2 to about 6 mm.

3. The anchor of claim 1, wherein a width of the second trailing end is about 1 mm to about 3 mm at its widest portion.

4. The anchor of claim 1, wherein the first, leading end is tapered.

5. The anchor of claim 4, wherein the first, leading end extends into a blunt tip having a continuous surface.

6. The anchor of claim 1, wherein the suture channel has a chamfered rim.

7. The anchor of claim 1, wherein the suture channel has a smooth rim.

8. The anchor of claim 1, wherein the flared portion has a shape effective to penetrate into bone.

9. The anchor of claim 8, wherein the flared portion includes a sharp edge.

10. The anchor of claim 8, wherein the flared portion includes a flat, bone-contacting face with a knife edge.

11. The anchor of claim 1, further including an insertion tool engaging bore extending into the elongate body from the second trailing end thereof.

12. The anchor of claim 1, wherein the elongate body is formed with a blue dye for visualization.

13. A system for anchoring tissue to a bone, comprising:
   a bioabsorbable suture anchor having:
      an elongate body defined by a longitudinal axis of symmetry, a first leading end and a second, trailing end, the elongate body comprising two opposed surfaces between the first and second ends, and a plurality of sidewalls extending between the two opposed surfaces;
      a bore extending into the elongate body from the second trailing end thereof;
      a flared portion formed on the second end and extending from one of the sidewalls, the flared portion being adapted to engage and anchor into bone tissue, wherein the suture anchor is configured to toggle and anchor inside a bone cavity based on tension being applied to a suture in the suture channel; and
      a suture channel formed in the elongate body for passage of a suture strand therethrough, the suture channel extending between the two opposed surfaces, being oriented substantially transverse at right angles to the longitudinal axis of symmetry of the body, and having a centerline that is transverse to and laterally offset with respect to the longitudinal axis of symmetry of the body in a direction opposite to the direction of the flared portion;
   a length of suture thread attached to the suture anchor; and
   a suture anchor insertion tool, the tool having an elongate member with a proximal, handle end and a distal, attachment end.

14. The system of claim 13, wherein the proximal, attachment end of the suture anchor insertion tool includes an insertion tip configured to provide an interference fit with the bore of the suture anchor.

15. The system of claim 13, wherein a length of the elongate body is in the range of about 2 to about 6 mm.

16. The system of claim 13, wherein a width of the second trailing end is about 1 mm to about 3 mm at its widest portion.

17. A method of attaching tissue to a bone in a patient's body, comprising the steps of:
   providing a system for anchoring tissue to bone, the system including a bioabsorbable suture anchor having an elongate body defined by a longitudinal axis of symmetry, a first leading end and a second, trailing end, the elongate body comprising two opposed surfaces between the first and second ends, and a plurality of sidewalls extending between the two opposed surfaces, a flared portion formed on the second end and extending from one of the sidewalls, the flared portion being adapted to engage and anchor into bone tissue, wherein the suture anchor is configured to toggle and anchor inside a bone cavity, and a suture channel formed in the elongate body for passage of a suture strand therethrough, the suture channel extending between the two opposed surfaces, being oriented substantially transverse at right angles to the longitudinal axis of symmetry of the body, and having a centerline that is transverse to and laterally offset with respect to the longitudinal axis of symmetry of the body in a direction opposite to the direction of the flared portion, the system further including a length of suture thread attached to the suture anchor;
   forming a bone cavity in the bone where the tissue is to be anchored;
   securing the suture strand to a portion of tissue to be attached to the bone;
   inserting the suture anchor at least partially within the bone cavity; and
   toggling the suture anchor by pulling on the attached suture strand such that the flared portion of the anchor penetrates into an inner surface of the bone cavity.

* * * * *